United States Patent
Fridman et al.

(10) Patent No.: US 8,388,618 B2
(45) Date of Patent: Mar. 5, 2013

(54) CONTROL OF MUCUS MEMBRANE BLEEDING WITH COLD PLASMA

(75) Inventors: Gregory Fridman, Philadelphia, PA (US); Alexander Fridman, Philadelphia, PA (US); Alexander F. Gutsol, San Ramon, CA (US); Gennady Friedman, Richboro, PA (US); David Staack, College Station, TX (US); Richard J. Hamilton, Jenkintown, PA (US)

(73) Assignees: Drexel University, Philadelphia, PA (US); Philadelphia Health & Education Corporation, Philadelphia, PA (US)

( * ) Notice: Subject to any disclaimer, the term of this patent is extended or adjusted under 35 U.S.C. 154(b) by 1119 days.

(21) Appl. No.: 12/175,756

(22) Filed: Jul. 18, 2008

(65) Prior Publication Data

US 2009/0054896 A1 Feb. 26, 2009

Related U.S. Application Data

(63) Continuation-in-part of application No. 11/911,479, filed as application No. PCT/US2006/015380 on Apr. 25, 2006.

(60) Provisional application No. 60/674,507, filed on Apr. 25, 2005.

(51) Int. Cl.
*A61B 18/18* (2006.01)
(52) U.S. Cl. .......... 606/49; 606/40; 606/41; 607/99
(58) Field of Classification Search .......... 435/173.1; 604/6.04, 20, 24, 26, 35; 606/34–51; 607/99
See application file for complete search history.

(56) References Cited

U.S. PATENT DOCUMENTS

| | | | |
|---|---|---|---|
| 3,838,242 A | 9/1974 | Goucher | |
| 3,903,891 A | 9/1975 | Brayshaw | |
| 5,683,366 A | 11/1997 | Eggers et al. | |
| 6,056,747 A * | 5/2000 | Saadat et al. | 606/50 |
| 6,099,523 A * | 8/2000 | Kim et al. | 606/40 |
| 6,213,999 B1 | 4/2001 | Platt, Jr. et al. | |
| 6,416,508 B1 | 7/2002 | Eggers et al. | |
| 6,482,201 B1 * | 11/2002 | Olsen et al. | 606/41 |
| 6,565,558 B1 | 5/2003 | Lindermeier et al. | |
| 6,629,974 B2 | 10/2003 | Penny | |

(Continued)

FOREIGN PATENT DOCUMENTS

| WO | WO 2004/105810 A1 | 12/2004 |
|---|---|---|
| WO | WO 2006/116252 | 11/2006 |

(Continued)

OTHER PUBLICATIONS

Brown, I.G., et al., "Growth of large patterned arrays of neurons using plasma methods," Plasma Physics and Controlled Fusion, 2003, 45(5), 547-554.

(Continued)

*Primary Examiner* — Nicholas Lucchesi
*Assistant Examiner* — Gerald Landry, II
(74) *Attorney, Agent, or Firm* — Woodcock Washburn, LLP (57) ABSTRACT

The use of non-thermal plasma to treat mucus membrane bleeding is described herein. A non-thermal plasma is generated using an apparatus having a first electrode that receives alternating electrical potentials from a power supply. When placed in an appropriate location proximate to tissue, a non-thermal plasma is generated, the second electrode being human tissue, blood, etc. To reduce the likelihood of an arc being generated, potentially causing tissue damage or pain, the first electrode is partially encapsulated by a dielectric. The non-thermal plasma is applied to the area of bleeding for treatment.

17 Claims, 8 Drawing Sheets

U.S. PATENT DOCUMENTS

| | | | |
|---|---|---|---|
| 6,723,091 B2* | 4/2004 | Goble et al. | 606/41 |
| 2001/0020167 A1* | 9/2001 | Woloszko et al. | 606/45 |
| 2001/0034519 A1* | 10/2001 | Goble et al. | 606/41 |
| 2002/0026186 A1* | 2/2002 | Woloszko et al. | 606/41 |
| 2004/0054366 A1 | 3/2004 | Davison et al. | |
| 2005/0118350 A1 | 6/2005 | Koulik et al. | |
| 2005/0259933 A1* | 11/2005 | Temelkuran et al. | 385/123 |
| 2006/0009763 A1 | 1/2006 | Goble et al. | |
| 2006/0084158 A1* | 4/2006 | Viol | 435/173.1 |
| 2006/0149129 A1 | 7/2006 | Watts et al. | |
| 2006/0293653 A1* | 12/2006 | Van Wyk | 606/41 |
| 2007/0213700 A1* | 9/2007 | Davison et al. | 606/32 |
| 2010/0010485 A1* | 1/2010 | West, Jr. | 606/37 |
| 2010/0145253 A1 | 6/2010 | Gutsol et al. | |
| 2011/0022043 A1* | 1/2011 | Wandke et al. | 606/41 |

FOREIGN PATENT DOCUMENTS

| WO | WO2006/116252 A2 | 11/2006 |
|---|---|---|
| WO | WO 2010/009103 | 1/2010 |

OTHER PUBLICATIONS

Chu, P.K., et al., "Plasma surface modification of biomaterials," Material Science and Engineering, 2002, R36, 143-206.

Fridman, G., et al., "Bio-medical applications of non-thermal atmospheric pressure plasma", Plasma Medicine Lab, Drexel Plasma Institute, Drexel University, Philadelphia, Pennsylvania, 5 pages.

Fridman, A., et al., "From plasma biology to plasma medicine: sterization, tissue engineering treatment of surface wounds and skin disease," The 58th Annual Gaseous Electronics Conference, Oct. 16-20, 2005.

Fridman, G., et al. "Use of non-thermal atmospheric pressure plasma discharge for coagulation and sterilization of surface wounds," ISPC-17, Toronto, Canada, Aug. 7-12, 2005, 1066-1067 and 665.

Ginsberg, G.G., "The argon plasma coagulator," Gastrointestinal Endoscopy, 2002, 55(7), 807-810.

Moisan, M., et al., "Plasma sterilization, methods mechanisms," Pure and Applied Chemistry, 2002, 74(3), 349-358.

Raiser, J., et al., "Argon plasma coagulation for open surgical applications:state of the art", J. Phys. D: Appl. Phys. 39, (2006), pp. 3520-3523.

Stoffels, E., "Biomedical applications of electric gas discharge," High Temperature Material Processes, Need Year, 5(2), 191-202.

Vasilets, V.N., et al., "The study of the action of high frequency discharge plasma on polyethylene surface," High Energy Chemistry, 1978, 12(N5), 442-447.

International Patent Application No. PCT/US2009/050509: International Search Report dated Feb. 23, 2010, 13 pages.

Kalghatgi, et al., "Mechanism of Blood Coagulation by Nonthermal Atmospheric Pressure Dielectric Barrier Discharge Plasma," IEEE Transactions on Plasma Science, Oct. 2007, 35, 5, 1559-1566.

* cited by examiner

CONTROL OF MUCUS MEMBRANE BLEEDING WITH COLD PLASMA

CROSS REFERENCE TO RELATED APPLICATIONS

This application is a continuation-in-part of U.S. patent application Ser. No. 11/911,479, filed Sep. 24, 2009, which is a national stage entry of PCT/US2006/015380, filed Apr. 25, 2006, which claims priority to U.S. Patent Application Ser. No. 60/674,507, filed Apr. 25, 2005.

STATEMENT OF GOVERNMENT RIGHTS

This invention was made with U.S. Government support under Contract Nos. W81XWH-04-1-0419 and W81XWH-05-2-0068 awarded by the U.S. Army (MRMC). The government has certain rights in the disclosed invention(s).

FIELD OF THE INVENTION

The present subject matter is related to the control of mucus membrane bleeding of the aerodigestive and gastrointestinal tract.

BACKGROUND

Mucus membrane bleeding of the aerodigestive and gastrointestinal tracts may occur for various reasons. Epistaxis, for example, is a hemorrhage in the nostril cavity. Common treatment of the epistaxis may include the application of direct pressure by pinching the flexible portion of the nose. Another treatment is the application of a vasoconstrictive agent. Other forms of the treatment of epistaxis may include cauterizing of the wound area in the nose with the application of thermal energy, or heat. These thermal methods, along with other methods described herein and used currently, including the use of devices such as the Bovie device, may cause tissue damage and be painful for the patient.

SUMMARY

The present subject matter is directed to the control of mucus membrane bleeding of the aerodigestive and gastrointestinal tracts using a non-thermal plasma. A device is described having an electrode connected to a power supply. In one exemplary embodiment, the electrode is partially encapsulated with a dielectric insulator. The device is configured to cause the generation of a non-thermal plasma when electrical power is applied to the electrode. The non-thermal plasma is placed at least partially in contact with the area of bleeding, causing coagulation of the blood.

In one aspect, an apparatus for treating mucus membrane bleeding is disclosed. The apparatus has a first electrode that receives power from an alternating current power supply. The power supply supplies voltage of alternating electrical potential to generate a non-thermal plasma at a location on the first electrode. The apparatus is at least partially encapsulated by a dielectric.

In another aspect, a system is described, the system having an apparatus having a first electrode and a dielectric partially encapsulating the first electrode. The apparatus is in electrical communication with the apparatus to provide alternating electrical potential to the apparatus to generate a non-thermal plasma.

Another aspect described is a method for treating mucus membrane bleeding. An apparatus is position in an appropriate location to a surface, typically the area in which bleeding is occurring. Alternating electrical potential is applied to the apparatus, which has an electrode, is supplied to the electrode to form an non-thermal plasma. The area is treated using the non-thermal plasma.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Other features of the subject matter are described below.

BRIEF DESCRIPTION OF THE DRAWINGS

The summary, as well as the following detailed description, is further understood when read in conjunction with the appended drawings. For the purpose of illustrating the subject matter, there are shown in the drawings exemplary embodiments of the subject matter; however, the presently disclosed subject matter is not limited to the specific methods, compositions, and devices disclosed. In addition, the drawings are not necessarily drawn to scale. In the drawings.

DETAILED DESCRIPTION OF ILLUSTRATIVE EMBODIMENTS

The present subject matter can be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The term "non-thermal plasma" is used in the present subject matter as is understood by those skilled in the art. Non-thermal plasma discharge is similar to dielectric barrier discharge ("DBD"). Although not limited to any particular configuration, the presently disclosed subject matter can be used in conjunction with a non-thermal plasma created at or near standard atmospheric pressure and does not need or create high, or tissue damaging, temperatures at the treatment location. In one example, when placed in contact with a non-thermal plasma, the tissue may increase in temperature by only a few degrees.

In the presently disclosed subject matter, an exemplary non-thermal plasma is an alternating current discharge between two electrodes, one of which is at least partially encapsulated by a dielectric. The other electrode, which is termed a floating electrode, is the tissue. Upon the application of an alternating potential to the encapsulated electrode, a plasma develops in the discharge gap, i.e. the space between the two electrodes. The non-thermal plasma is driven by an applied alternating high voltage, some examples, kilovolts, which generates a high electric field between the electrodes. The dielectric preferable prevents arcing between the two electrodes, which may cause thermal damage to tissue that comes in contact with the arc.

In the present subject matter, the dielectric helps to prevent arc formation by providing for the accumulation of charges on the surfaces, thereby generating an electric field that opposes the applied field, thereby limiting the current and preventing an uncontrolled discharge from occurring. The alternating high voltage polarities help to ensure the formation of a discharge in each half of the cycle. The frequency of applied potential may vary, but an exemplary frequency can be in the kilohertz range. This frequency may help to prevent the plasma generated in each half of the cycle from fully extinguishing, i.e. appears to be a constant and steady-state plasma.

Figure 1:
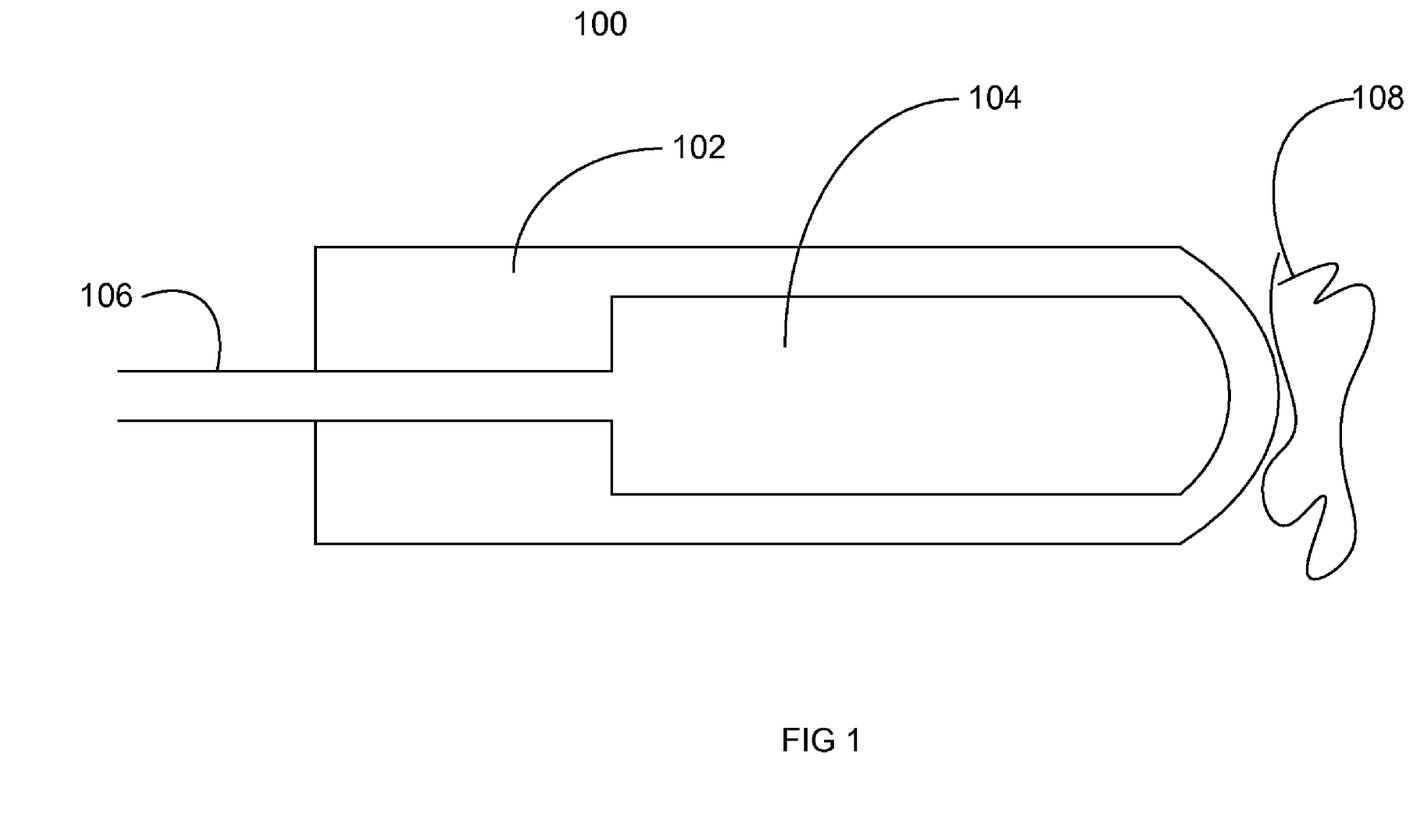
FIG. 1 is an exemplary and non-limiting illustration of an apparatus for controlling mucus membrane bleeding of the aerodigestive and gastrointestinal tracts.

Referring now to the drawings, wherein like reference numerals designate corresponding structure throughout the views, and referring in particular to FIG. 1, an exemplary illustration of an apparatus, apparatus 100, for treating mucus membrane bleeding of the aerodigestive and gastrointestinal tracts is described. Apparatus 100 has electrode 104 which is in electrical communication with an external power supply (not shown) through electrical connection 106. To provide for the creation of non-thermal plasma 108, electrode 104 is at least partially encapsulated by dielectric 102. Dielectric 102 can be constructed from various materials including plastic or ceramic. Further, the rigidity of dielectric 102 may vary from rigid, or non-flexible, to flexible.

Figure 2:
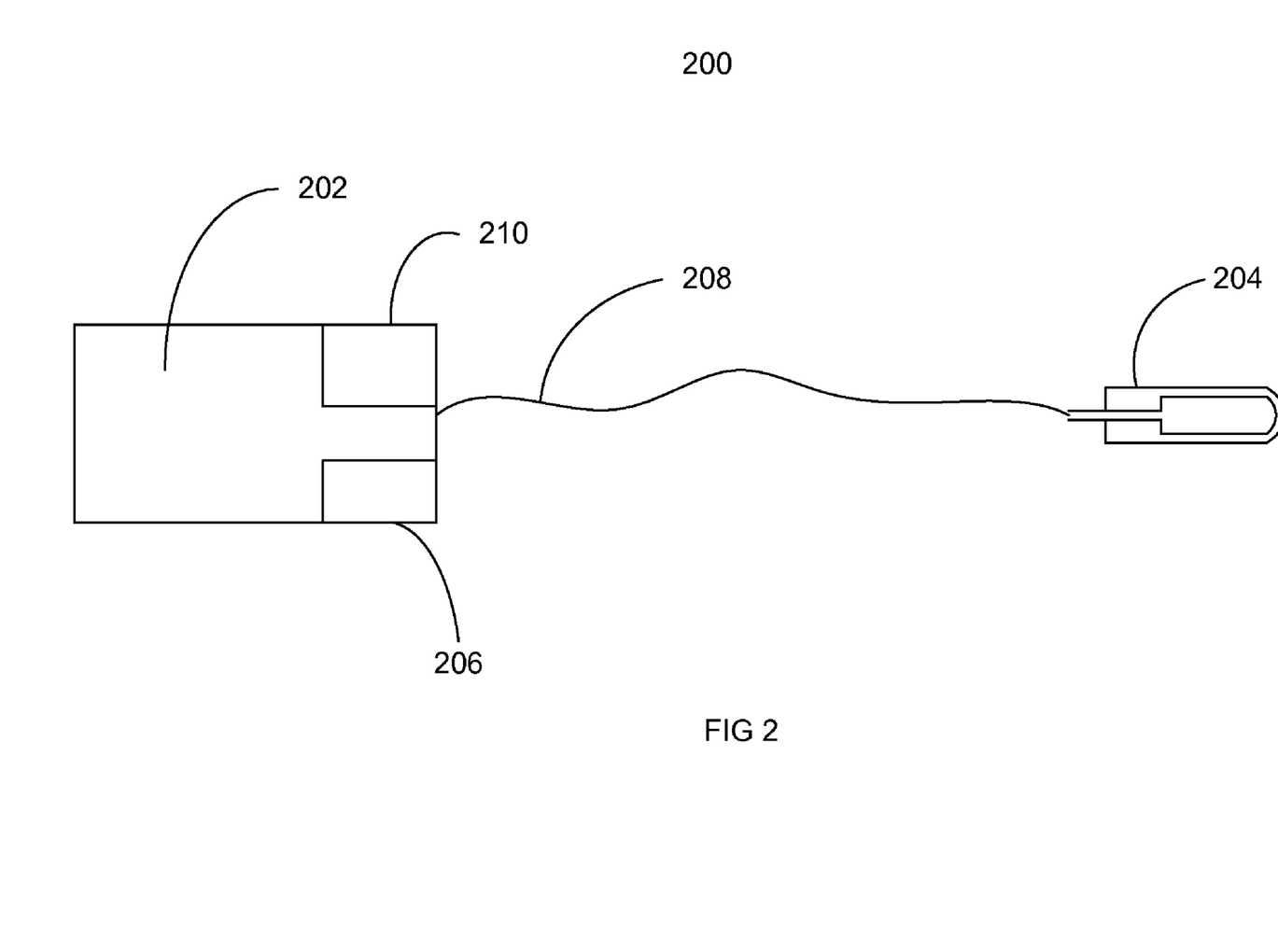
FIG. 2 is an exemplary and non-limiting illustration of a system for controlling mucus membrane bleeding of the aerodigestive and gastrointestinal tracts.

FIG. 2 illustrates exemplary system 200 for controlling mucus membrane bleeding of the aerodigestive and gastrointestinal tracts. System 200 comprises apparatus 204 which is constructed in a similar manner to apparatus 100 of FIG. 1. To power apparatus 204, apparatus 204 is connected to power supply 202 via electrical connector 208. Power supply 202 may have various control or monitoring features such as power monitor 210 and power control 206.

Power supply 202 may have additional control features such as frequency control. In one exemplary embodiment, non-thermal plasma is generated by system 200 using a high frequency oscillation from about 5 kHz to about 20,000 kHz. A preferable range, depending upon various conditions, can be from about 10 kHz to approximately 30 kHz. Power supply 202 may also be configured to output high voltage from approximately 2 kV to about 50 kV. Depending upon various conditions, a preferable range of voltage can be from 10 kV to approximately 30 kV.

Figure 3:
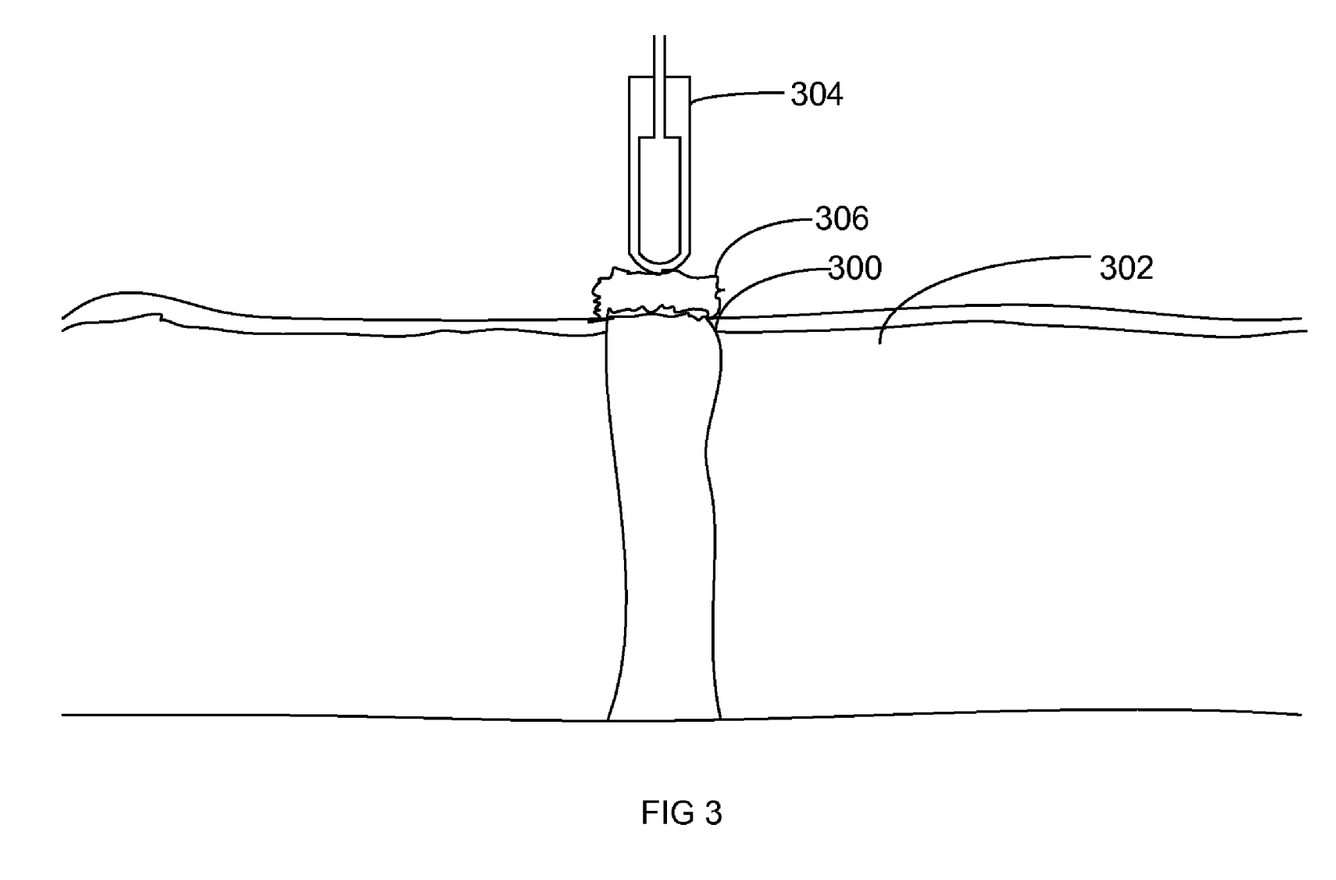
FIG. 3 is an exemplary and non-limiting illustration of an apparatus controlling a bleed using plasma.

By placing apparatus 204 in a suitable position proximate to tissue, a non-thermal plasma can be created, as shown in FIG. 3. Apparatus 304, configured in a manner similar to apparatus 100 of FIG. 1, is placed in a location proximate to tissue 302. In this example, capillaries (not shown) in tissue 302 are damaged, causing local bleeding region 300 to occur in tissue 302. Apparatus 304 is placed in a location proximate to tissue 302 and local bleed region 300. When power is supplied to apparatus 304, non-thermal plasma 306 is generated, as the surface of tissue 302 acts as a second electrode. To treat the bleeding, apparatus 304 is moved to place non-thermal plasma 306 in contact with local bleeding region 300. This causes the blood to coagulate to arrest or control the bleeding.

The present subject matter can be used to control or treat bleeding in various locations of the mucus membrane of the aerodigestive and gastrointestinal tracts. The detailed description below discusses the use of the subject matter in treating epistaxis, or nose bleeds, for exemplary purposes only and is not intended to limit the scope of the present subject matter to epistaxis.

Figure 4:
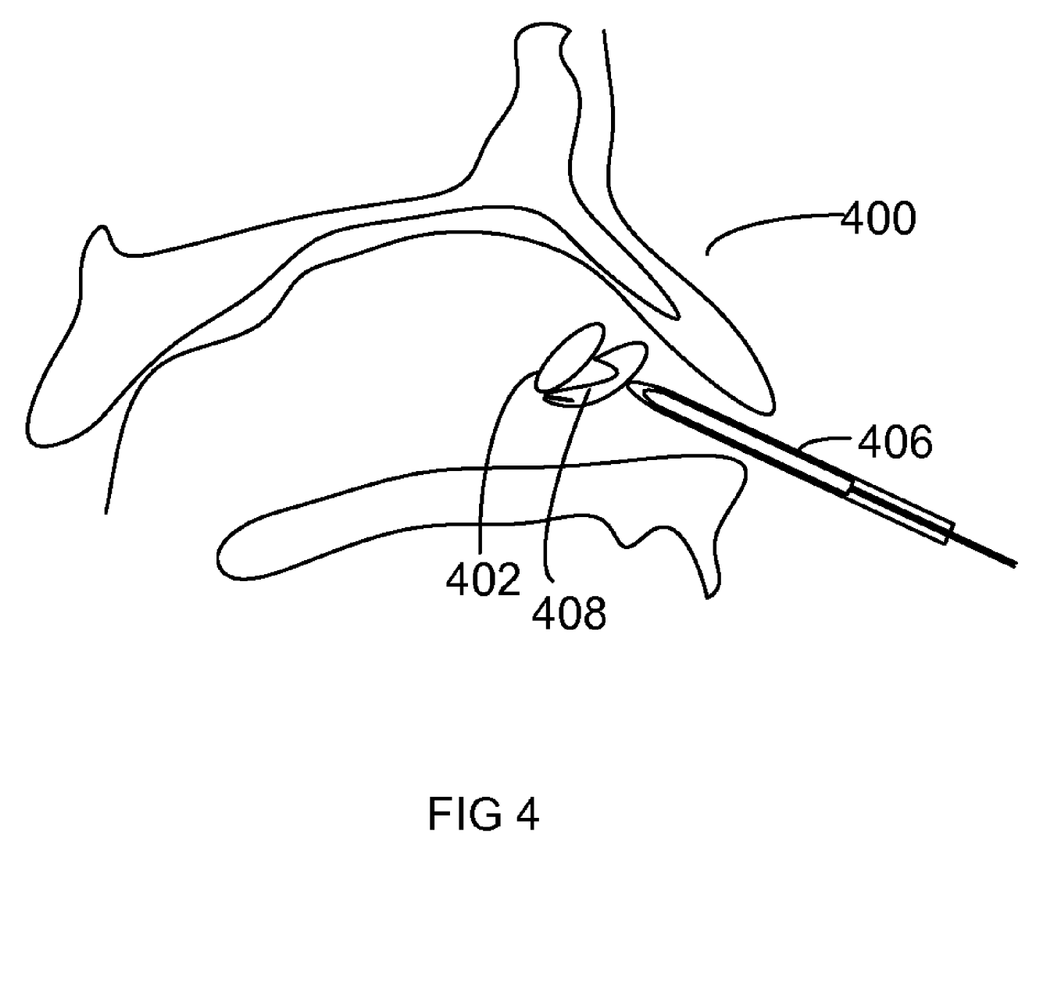
FIG. 4 is an exemplary and non-limiting illustration of an apparatus controlling a nose bleed.

FIG. 4 illustrates the use of non-thermal plasma to control epistaxis. In FIG. 4, nasal cavity 400 is shown to have epistaxis 402, which may have occurred for various reasons. Apparatus 406, having construction similar to apparatus 100 of FIG. 1, is placed in a location proximate to epistaxis 402. The tissue surrounding epistaxis 402 and the epistaxis itself acts as a second electrode. When in a suitable position, alternating potential applied to apparatus 406 creates non-thermal plasma 408, wherein the non-thermal plasma 408 effectively completes an electrical circuit between a first potential applied to apparatus 406 and epistaxis 402 and surrounding tissue. Apparatus 406 can be moved to place non-thermal plasma 408 in contact with epistaxis 402, causing the coagulation of blood in epistaxis 402, thereby controlling the bleeding. The application time, i.e. the time in which non-thermal plasma 408 is placed in contact with epistaxis 402, may vary according to various conditions, such as the amount of bleeding, the size of epistaxis 402, the number of capillaries that are bleeding, and the power supplied to apparatus 406.

Figure 5:
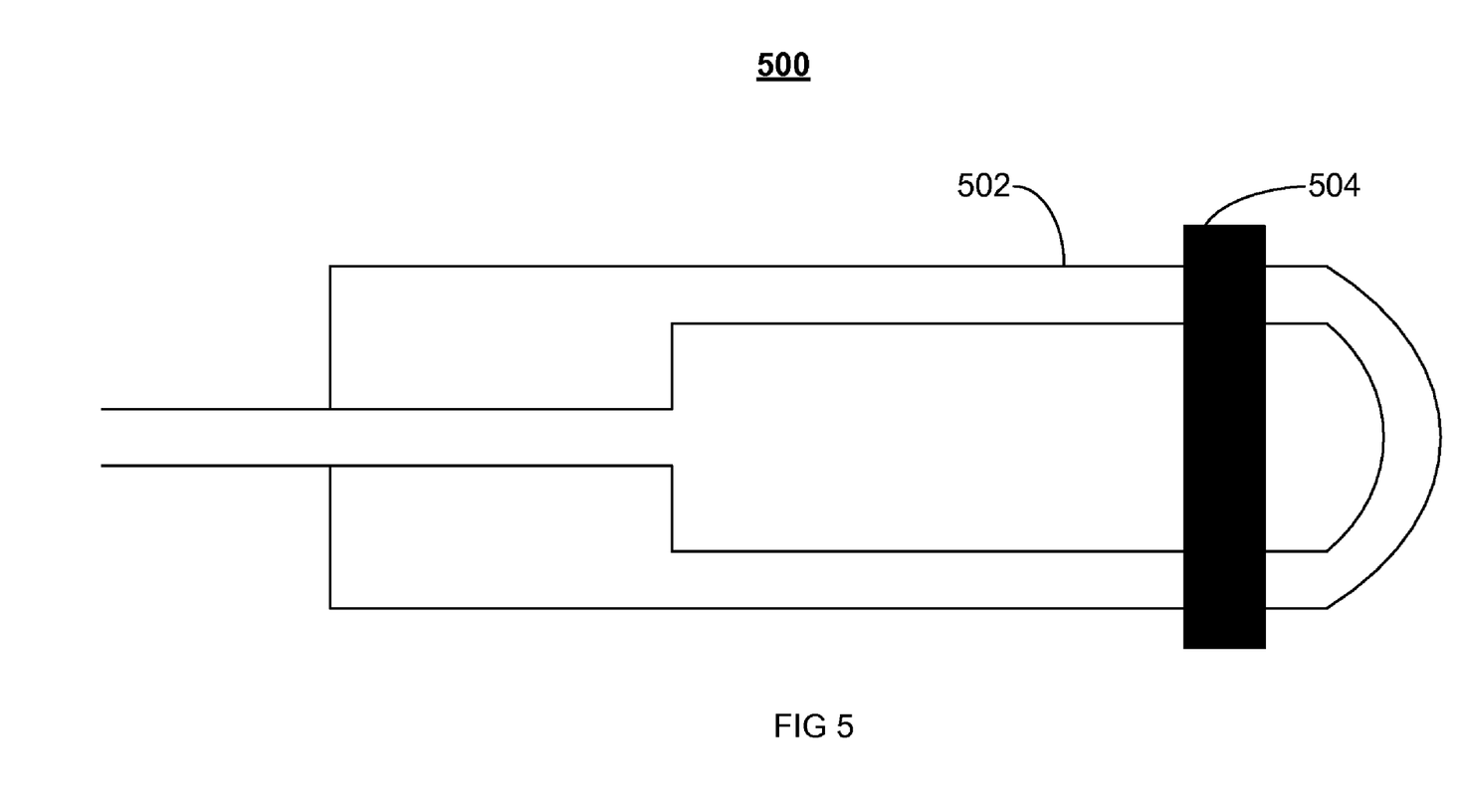
FIG. 5 is an exemplary and non-limiting illustration of an alternative apparatus for controlling epistaxis.

To help position apparatus 406 within the nasal cavity, to prevent contact of apparatus 406 with the tissue in the nasal cavity, or for other reasons not disclosed herein, apparatus 406 can be configured with an external piece. For example, apparatus 500 shown in FIG. 5, which can be similar in construction to apparatus 100 of FIG. 1, can be constructed having o-ring 504 that is positioned circumferentially around the outer circumference of dielectric 502 of apparatus 500. O-ring 504 may help to position apparatus 500 as well as help to keep the end of apparatus 500 that is inserted into a nasal cavity from contacting tissue in the nasal cavity.

Figure 6:
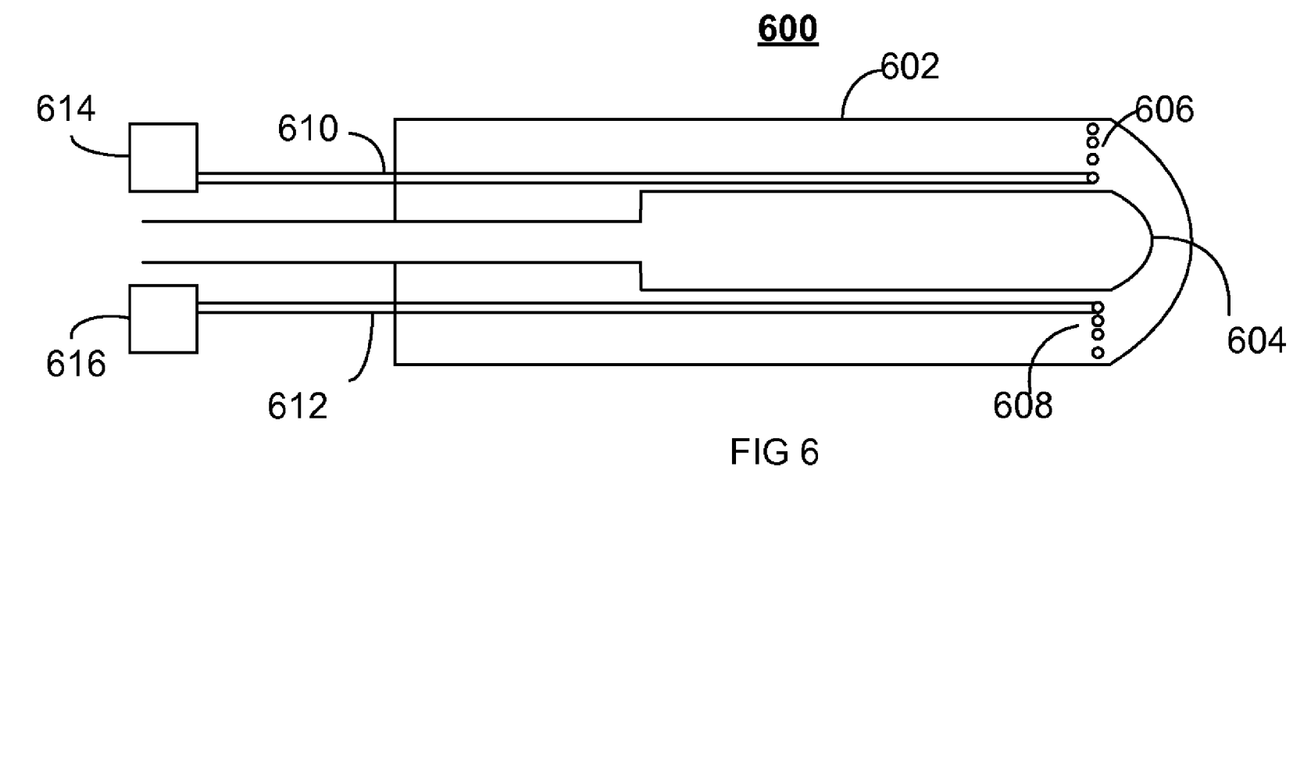
FIG. 6 is an exemplary and non-limiting illustration of a further alternative apparatus for controlling epistaxis using an air source and a vacuum.

If there is extensive bleeding, or if the bleeding is severe enough that the site of the epistaxis is not suitable for contact by a non-thermal plasma, an apparatus for generating the non-thermal plasma can be further configured to have additional features that help make the site suitable for treatment. FIG. 6 is an illustration of apparatus 600, which can be used in a manner similar to apparatus 100 of FIG. 1, that can be used to assist in the treatment of the epistaxis.

Apparatus 600 has dielectric 602 which encapsulates electrode 604 which is in electrical communication with a power supply (not shown). To assist in removing particles, debris or blood from the area, apparatus 600 can be configured to have additional features. In FIG. 6, apparatus has vacuum lines 606, which are connected to vacuum source 614 through tube 610. By applying a vacuum generated by vacuum source 614 to the area, a person using apparatus 600 can remove material from the area through vacuum lines 606. This may provide the ability to make the area suitable for application of a plasma.

To provide for additional benefits, apparatus 600 may also be supplied with a pressurized gas source to forcibly remove material from the area being treated. Apparatus 600 is shown having pressure lines 608 which provide for the expelling of pressurized gas. Pressure lines 608 are connected to pressurized gas source 616 through tube 612. The gas used may vary depending upon a particular need or configuration, but may include air or hydrogen. The gas may also be a local anesthetic. Both the vacuum in vacuum lines 606 and the pressurized gas in pressure lines 608 can be controlled through various means, such as a shutoff or throttle valve (not shown).

Figure 7:
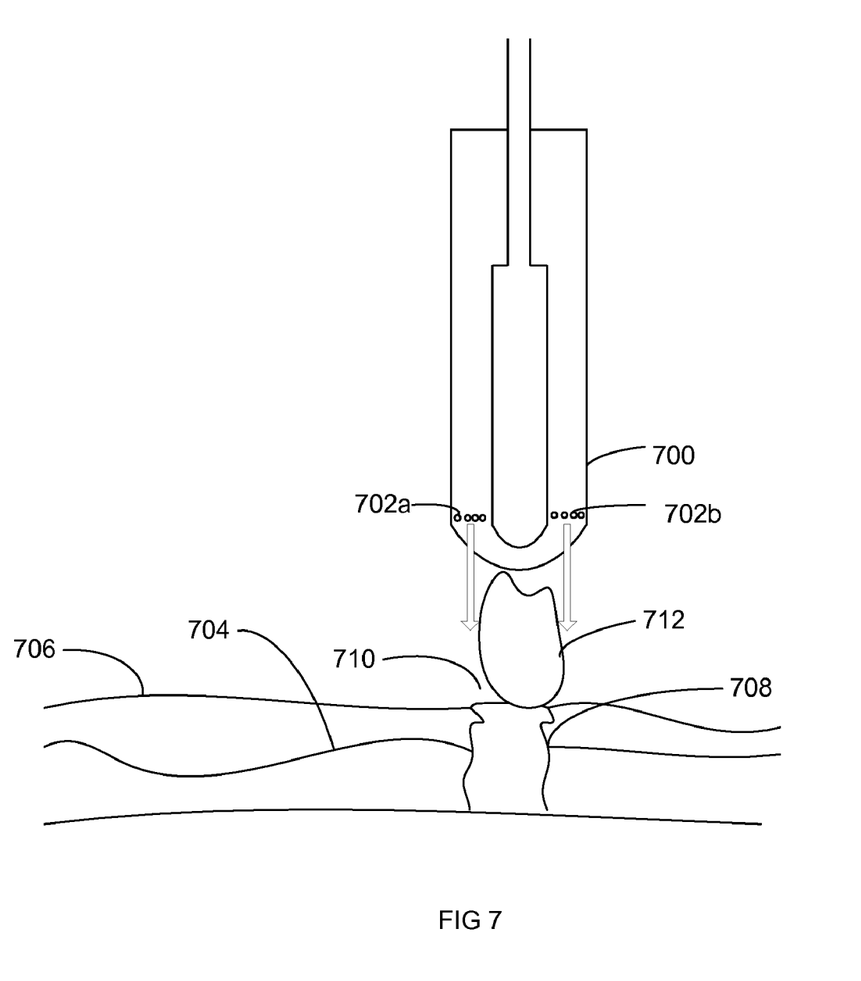
FIG. 7 is an exemplary and non-limiting illustration of a still further alternate apparatus for controlling epistaxis assisted by gas flow pressure.

If the epistaxis is severe enough that the application of plasma does not abate the flow of blood through coagulation, apparatus 100 can be configured to provide a gas-dynamic pressure source that counteracts the pressure of the blood exiting the wound site. Shown in FIG. 7 is apparatus 700, which operates and can be constructed in a manner similar to apparatus 100 of FIG. 1. A user (not shown) may attempt to use apparatus 700 to control epistaxis 708, which is allowing blood from capillary 704 to escape through tissue 706.

Because blood in capillary 704 can be at blood pressure, the rate at which the blood exits epistaxis 708 at exit point 710 may be too great to allow blood coagulation, even with the application of non-thermal plasma 712 generated through the use of apparatus 700. The rate at which blood exits epistaxis 708 depends, at least in part, upon the relative pressure between the pressure of the blood in capillary 704 and atmosphere, or the pressure at exit point 710. It is understood that other factors may affect the rate at which the blood exits, including the size of epistaxis 708.

Because it may not be feasible to change the pressure of a patient's blood system, it may be necessary to change the pressure at exit point 710. Thus, apparatus 700 can be configured to apply an additional pressure in the form of directional gas flow to provide a counteracting pressure to the pressure in capillary 704 to try to reduce the rate of blood flow in epistaxis 708. Apparatus 700 is configured to have gas jets 702a and 702b. Gas jets 702a and 702b can be configured to have directional outlets that expel pressurized gas in a specific direction. The directional pressurized gas can be used to provide the counteracting pressure discussed previously. Depending upon the severity of the blood flow, the rate and speed of gas exiting gas jets 702a and 702b can be adjusted. Further, depending upon a particular configuration, the gas may vary, from air to an anesthetic.

Figure 8:
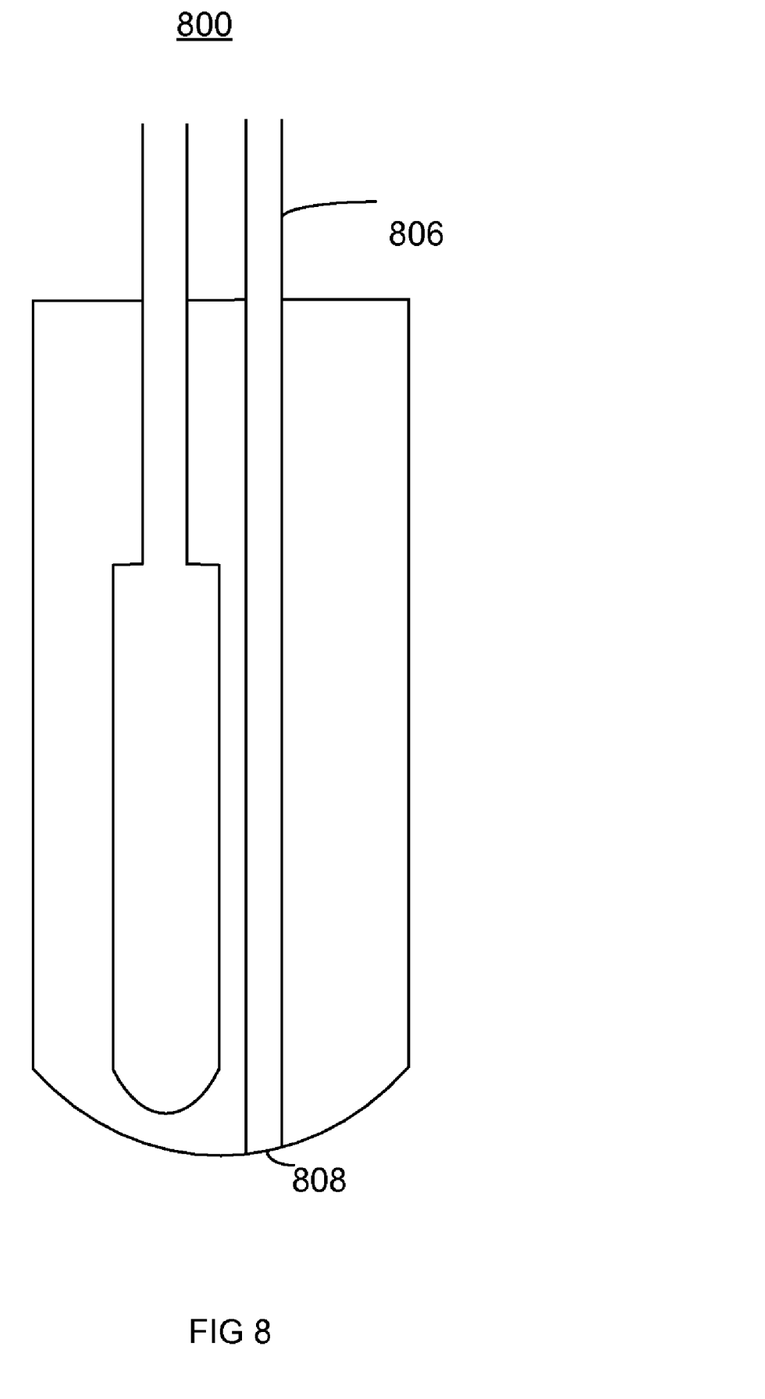
FIG. 8 is an exemplary and non-limiting illustration of an apparatus for controlling epistaxis using optics.

To assist the user in correct placement of the plasma, the user can be provided with optics that may permit the user to see the area of application and the effect of the treatment of the plasma, among other benefits. FIG. 8 is an exemplary and non-limiting illustration of an apparatus for controlling epistaxis using optics. Apparatus 800 can be constructed and operated in a manner similar to apparatus 100 of FIG. 1 with some additional features. To provide for optical input for the user, apparatus 800 can be configured to have fiberoptic waveguide 806 which transmits images received at optical input 808 to the user (not shown). The input may provide the user with the ability to properly position apparatus 800 to treat an epistaxis. The optic may also include a light source to illuminate the area undergoing treatment.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment but rather should be construed in breadth and scope in accordance with the appended claims.

What is claimed:

1. An apparatus for treating mucus membrane bleeding of the aerodigestive and gastrointestinal tracts, comprising:
    a first electrode configured to receive power from an alternating current power supply, wherein the power supply is configured to supply a voltage of alternating electrical potential to generate a non-thermal plasma in a location proximate to the first electrode, wherein the non-thermal plasma that is generated is capable of being placed in an appropriate location to an area in which a mucus membrane is bleeding; and
    a dielectric at least partially encapsulating the first electrode, wherein the dielectric is configured to reduce the likelihood of an arc when a plasma is formed;
    a fiberoptic waveguide to transmit images to a user of the apparatus; and:
    (a) a vacuum line to provide for a vacuum, configured to remove particles, debris, blood, or any combination thereof; or
    (b) a pressure line to provide for a source of pressurized gas, configured to provide a positive pressure source to a site in which the mucus membrane is bleeding; or
    (c) both (a) and (b).

2. The apparatus of claim 1, wherein the first electrode or dielectric, or both, are flexible.

3. The apparatus of claim 1, wherein the first electrode or the dielectric, or both, are rigid.

4. The apparatus of claim 1, wherein the positive pressure source is used to remove material from the site.

5. The apparatus of claim 1, wherein the pressurized gas is expelled through a directional nozzle to provide for a gas jet, wherein the pressure of the gas jet is capable of being further configured to provide for a counteracting pressure to help reduce the rate of bleeding.

6. The apparatus of claim 1, wherein the power supply is capable of supplying a voltage in the range of from about 2 kV to about 50 kV.

7. The apparatus of claim 6, wherein the voltage of the power supply is in the range of from about 10 kV to about 30 kV.

8. The apparatus of claim 1, wherein the frequency of the power supply is in the range of from about 5 kHz to about 20,000 kHz.

9. The apparatus of claim 8, wherein the frequency of the power supply is in the range of from about 10 kHz to about 30 kHz.

10. The apparatus of claim 1, wherein the mucus membrane bleeding is an epistaxis.

11. A system, comprising:
    an apparatus comprising:
        a first electrode; and
        a dielectric at least partially encapsulating the first electrode, wherein the dielectric is configured to reduce the likelihood of an arc when a plasma is formed;
    a fiberoptic waveguide configured to provide for the transmission of images to a user of the apparatus;
    a vacuum source for providing a vacuum to a vacuum line of the apparatus;
    a pressurized gas source for providing a source of pressurized gas to a gas line of the apparatus; and an alternating current power supply in electrical communication with the first electrode, wherein the power supply is configured to supply a voltage of alternating electrical potential to generate a non-thermal plasma in a location proximate to the first electrode, wherein the non-thermal plasma that is generated is placed proximate to an area which is bleeding.

12. The system of claim 11, wherein the pressurized gas is expelled through a directional nozzle to provide for a gas jet, wherein the gas jet is capable of being configured to provide for a counteracting pressure to help reduce the rate of flow of blood.

13. The system of claim 11, wherein the voltage of the power supply is in a range from approximately 2 kV to approximately 50 kV.

14. The system of claim 13, wherein the voltage of the power supply is in a range from 10 kV to 30 kV.

15. The system of claim 11, wherein the frequency of the power supply is in a range from approximately 5 kHz to approximately 20,000 kHz.

16. The system of claim 11, wherein the frequency of the power supply is in a range from 10 kHz to 30 kHz.

17. The system of claim 11, wherein the mucus membrane bleeding is an epistaxis.

* * * * *